United States Patent [19]

Araki et al.

[11] Patent Number: 5,856,612
[45] Date of Patent: Jan. 5, 1999

[54] PROCESS FOR PRODUCING α-OLEFIN OLIGOMER

[75] Inventors: Yoshitaka Araki; Hirofumi Nakamura; Yoshiaki Nanba; Takeshi Okano, all of Okayama-ken, Japan

[73] Assignee: Mitsubishi Chemical Corporation, Japan

[21] Appl. No.: 790,479

[22] Filed: Jan. 29, 1997

[30] Foreign Application Priority Data

| Feb. 2, 1996 | [JP] | Japan | 8-17480 |
| Feb. 2, 1996 | [JP] | Japan | 8-017480 |
| Aug. 8, 1996 | [JP] | Japan | 8-226040 |
| Aug. 12, 1996 | [JP] | Japan | 8-212535 |

[51] Int. Cl.$^6$ ................... C07C 2/26; C07C 2/24
[52] U.S. Cl. ........... 585/522; 585/512; 585/513; 585/523; 585/527
[58] Field of Search .............. 585/512, 513, 585/522, 523, 527

[56] References Cited

U.S. PATENT DOCUMENTS

| 4,777,315 | 10/1988 | Levine et al. | 585/512 |
| 5,331,070 | 7/1994 | Pettijohn et al. | 526/105 |
| 5,345,023 | 9/1994 | Chauvin et al. | 585/527 |
| 5,491,272 | 2/1996 | Tanaka et al. | 585/520 |
| 5,523,507 | 6/1996 | Reagen et al. | 585/513 |

*Primary Examiner*—Hien Tran
*Assistant Examiner*—Thuan D. Dang
*Attorney, Agent, or Firm*—Nixon & Vanderhye

[57] ABSTRACT

The present invention relates to a process for producing an α-olefin oligomer by subjecting α-olefin to oligomerization in a reaction zone in the presence of a reaction solution containing a chromium-based catalyst, which comprises, continuously conducting said oligomerization of α-olefin by using said chromium-based catalyst comprising at least a chromium compound (a), a nitrogen-containing compound (b) selected from the group consisting of amines, amides and imides, and an alkyl aluminum compound (c) while maintaining a molar ratio of the α-olefin oligomer to α-olefin in the range of 0.05 to 1.00.

16 Claims, No Drawings

PROCESS FOR PRODUCING α-OLEFIN OLIGOMER

BACKGROUND OF THE INVENTION

The present invention relates to a process for producing an α-olefin oligomer, and more particularly relates to a process for producing an α-olefin oligomer comprising mainly of 1-hexene, from ethylene with a high yield and a high selectivity in an industrially useful manner.

It is hitherto known that a oligomerization of α-olefin such as ethylene is carried out in the presence of a chromium-based catalyst comprising a chromium compound and an organoaluminum compound in combination. For instance, Japanese Patent Publication (KOKOKU) No. 43-18707 discloses a production method of 1-hexene and polyethylene from ethylene by using a catalyst comprising a 6-Group transition metal such as chromium and polyhydrocarbyl-aluminum-oxide.

Further, Japanese Patent Application Laid-Open (KOKAI) No. 3-128904 discloses a trimerization method of an α-olefin by using a catalyst obtained by previously reacting a chromium-containing compound having a chromium-pyrrolyl bond with metal alkyl or a Lewis acid. Furthermore, Japanese Patent Application Laid-Open (KOKAI) No. 6-239920 discloses a oligomerization method of an α-olefin by using a catalyst obtained by mixing a chromium compound, a pyrrole-containing compound, a metal alkyl compound and a halide source with each other in a common solvent.

In addition, the present inventors have recently proposed, in Japanese Patent Application Laid-Open (KOKAI) No. 8-3216, an oligomerization method of an α-olefin by using a chromium-based catalyst comprising a chromium-containing compound, a pyrrole ring-containing compound, a metal alkyl compound and a halide source in combination in such a manner that the chromium-containing compound and the metal alkyl compound are kept in non-contact with each other until these compounds are brought into contact with an α-olefin. According to the afore-mentioned method, 1-hexene can be produced by subjecting α-olefin, particularly ethylene, to oligomerization in the presence of the catalyst having a high catalytic activity.

However, in any of these methods, a considerable amount of polymer as by-product have been inevitably produced. Such a production of the polymer as by-product causes problems such as adhesion of the polymer to an apparatus used, necessity of removing the polymer from a solution containing a reaction product, or the like. For these reasons, when it is intended to conduct the oligomerization of α-olefin in an industrially effective manner, it is important to reduce an amount of the by-product to as low a level as possible.

Further, in the method described in Japanese Patent Publication (KOKOKU) No. 43-18707, a large amount of polyethylene is produced simultaneously with the production of 1-hexene. In the case where the reaction condition is adjusted so as to reduce the amount of polyethylene as a by-product, there is caused a problem that a catalytic activity of the catalyst in the reaction system is deteriorated. In the method described in Japanese Patent Publication (KOKOKU) No. 3-128904, there arises a problem that an amount of the high-molecular weight polymer produced can be limited to a small level but a catalytic activity thereof is insufficient.

In addition, in the method described in the Japanese Patent Application Laid-Open (KOKAI) No. 6-239920, the catalytic activity is also insufficient from a standpoint of industrial-scale oligomerization of α-olefin, though the method exhibits a high selectivity for 1-hexene. Whereas, in the method described in the Japanese Patent Application Laid-Open (KOKAI) No. 8-3216, the selectivity for 1-hexene is insufficient, though the catalyst used in the method exhibits a sufficient catalytic activity to carry out the industrial-scale oligomerization of α-olefin.

As a results of the present inventors' earnest studies for solving the above problems, it has been found that by using the chromium-based catalyst formed from at least a chromium compound (a), a nitrogen-containing compound (b) selected from the group consisting of amines, amides and imides, and an alkyl aluminum compound (c) while maintaining a molar ratio of the α-olefin oligomer to α-olefin in the range of 0.05 to 1.00, an α-olefin oligomer such as 1-hexene can be produced with a high yield and high selectivity while extremely reducing an amount of polymer as by-product. The present invention has been based on this finding.

SUMMARY OF THE INVENTION

The object of the present invention is to provide a continuous process for producing an α-olefin oligomer such as 1-hexene with a high yield and a high selectivity while reducing an amount of polymer as by-product to an extremely low level.

To accomplish the aim, in an aspect of the present invention, there is provided a process for producing an α-olefin oligomer by subjecting an α-olefin to oligomerization in the presence of a reaction solution containing a chromium-based catalyst in the reaction zone, which comprises, continuously conducting the oligomerization of an α-olefin by using the chromium-based catalyst formed from at least a chromium compound (a), a nitrogen-containing compound (b) selected from the group consisting of amines, amides and imides, and an alkyl aluminum compound (c) while maintaining a molar ratio of the α-olefin oligomer to α-olefin in the range of 0.05 to 1.00.

DETAILED DESCRIPTION OF THE INVENTION

In the process according to the present invention, as the chromium-based catalyst, there may be used a catalyst formed from at least a chromium compound (a), one or more nitrogen-containing compound (b) selected from the group consisting of amines, amides and imides, and an alkyl aluminum compound (c).

The chromium compounds suitably used in the present invention are those expressed by the general formula of $CrX_n$, wherein X represents an optional organic or inorganic group or an anionic atom and n is an integer of 1 to 6, and when n is not less than 2, X may be same or different. A valence of chromium may be 0 to 6. It is preferred that n of the above-mentioned general formula is an integer of not less than 2.

As the organic groups as the X group of the afore-mentioned general formula, various groups generally having 1 to 30 carbon atoms can be suitably used. Specific examples of suitable organic groups may include hydrocarbon groups, carbonyl groups, alkoxy groups, carboxyl groups, β-diketonate groups, β-keto-carboxyl groups, β-keto-ester groups, amide groups or the like. Examples of the hydrocarbon groups may include alkyl groups, cycloalkyl groups, aryl groups, alkylaryl groups, aralkyl groups, a cyclopentadienyl group or the like. Examples of the inorganic groups as the X group of the afore-mentioned general formula may include chromate-forming groups such as a nitric group and a sulfuric group. Examples of the anionic atom as the X group of the afore-mentioned general formula may include oxygen, halogen or the like.

The above-defined chromium compounds may be alkoxy salts of chromium, carboxyl salts of chromium, β-diketonate salts of chromium, salts of chromium and an anion derived from β-keto-esters, or chromium halides. Specific examples of the chromium compounds may include chromium (IV)-tert-butoxide, chromium (III)-acetylacetonate, chromium (III)-trifluoro-acetylacetonate, chromium (III)-hexafluoro-acetylacetonate, chromium (III) (2,2,6,6-tetramethyl-3,5-heptane-dionate), $Cr(PhCOCHCOPh)_3$ (wherein Ph represents a phenyl group), chromium (II) acetate, chromium (III) acetate, chromium (III)-2-ethyl hexanoate, chromium (III) benzoate, chromium (III) naphthenate, $Cr(CH_3COCHCOOCH_3)_3$, chromium (II) chloride, chromium (III) chloride, chromium (II) bromide, chromium (III) bromide, chromium (II) iodide, chromium (III) iodide, chromium (II) fluoride, chromium (III) fluoride, or the like.

In addition, a complex comprising the afore-mentioned chromium compound and an electron donor is suitably used as the chromium compound. Such an electron donor may be selected from compounds containing nitrogen, oxygen, phosphorus or sulfur atom.

Examples of the nitrogen-containing electron donors may include nitrile, amine, amide, nitro compounds or the like. Specific examples of the nitrogen-containing electron donors may include acetonitrile, pyridine, dimethylpyridine, dimethyl-formamide, N-methyl-formamide, aniline, nitrobenzene, tetramethyl-ethylene-diamine, diethylamine, isopropyl-amine, hexamethyl-silazane, pyrrolidone or the like.

Examples of the oxygen-containing electron donors may include esters, ethers, ketones, alcohols, aldehydes or the like. Specific examples of the oxygen-containing electron donors may include ethyl acetate, methyl acetate, tetrahydrofuran, dioxane, diethyl ether, dimethoxy-ethane, diethylene glycol dimethyl ether, triethylene glycol dimethyl ether, acetone, methyl ethyl ketone, methanol, ethanol, acetaldehyde or the like.

Examples of the phosphorus-containing electron donors may include hexamethyl phosphoramide, hexamethylphosphorous triamide, triethyl phosphite, tributyl-phosphine-oxide, triethyl phosphine or the like. Examples of the sulfur-containing electron donors may include carbon disulfide, dimethyl sulfoxide, tetramethylene sulfone, thiophene, dimethyl sulfide or the like.

Examples of the complexes comprising the chromium compound and the electron donor may include ether complexes of chromium halide, ester complexes of chromium halide, ketone complexes of chromium halide, aldehyde complexes of chromium halide, alcohol complexes of chromium halide, amine complexes of chromium halide, nitrile complexes of chromium halide, phosphine complexes of chromium halide, thioether complexes of chromium halide, or the like. Specific examples of these complexes may include $CrCl_3.3THF$, $CrCl_3.3$ (dioxane), $CrCl_3.(CH_3CO_2n-C_4H_9)$, $CrCl_3.(CH_3CO_2C_2H_5)$, $CrCl_3.3$ (i-$C_3H_7OH$), $CrCl_3.3[CH_3(CH_2)_3CH(C_2H_5)CH_2OH]$, $CrCl_3.3$(pyridine), $CrCl_3.2$(i-$C_3H_7NH_2$), $[(CrCl_3.3CH_3CN].CH_3CN$, $CrCl_3.3PPh_3$, $CrCl_2.2THF$, $CrCl_2.2$(pyridine), $CrCl_2.2[(C_2H_5)_2NH]$, $CrCl_2.2CH_3CN$, $CrCl_2.2[P(CH_3)_2Ph]$ or the like. Incidentally, in the above specific examples of the complexes, "THF" means tetrahydrofuran.

It is preferred that the chromium compound be soluble in a hydrocarbon solvent. Examples of such chromium compounds may include salts of chromium and β-diketonate, salts of chromium and carboxylic acid, salts of chromium and an anion derived from β-keto-esters, salts of chromium and β-keto-carboxylic acid, amide complexes of chromium, carbonyl complexes of chromium, carbene complexes of chromium, cyclopentadienyl complexes of chromium, alkyl complexes of chromium, phenyl complexes of chromium or the like.

Specific examples of various chromium-containing complexes such as the carbonyl complexes of chromium, the carbene complexes of chromium, the cyclopentadienyl complexes of chromium, the alkyl complexes of chromium and the phenyl complexes of chromium may include $Cr(CO)_6$, $(C_6H_6)Cr(CO)_3$, $(CO)_5Cr(=CCH_3(OCH_3))$, $(CO)_5Cr(=CC_6H_5(OCH_3))$, $CpCrCl_2$ (wherein Cp represents a cyclopentadienyl group), $(Cp*CrClCH_3)_2$ (wherein Cp* represents a pentamethyl-cyclopentadienyl group), $(CH_3)_2CrCl$ or the like.

The chromium compound may be supported on a carrier such as an inorganic oxide. However, it is suitable to combine the chromium compound with any other catalytic components without carrying it on the carrier. That is, in accordance with the present invention, it is preferred that the chromium-based catalyst is prepared by a particular method as described hereinafter. In such a method, it has been found that the chromium compound exhibits a high catalytic activity even though it is not supported on the carrier. Further, in the case where the chromium compound is used without being supported on the carrier, complicated operations required for supporting the compound on the carrier can be omitted. Furthermore, undesirable increase in a total amount of the catalyst used (a sum of the carrier and the catalytically active components) is effectively avoided.

The amines used as the nitrogen-containing compound (b) in the present invention may be primary amines, or secondary amines. Examples of the primary amines may include ethylamine, isopropylamine, cyclohexylamine, benzylamine, aniline, naphthylamine or the like. Examples of the secondary amines may include diethylamine, diisopropylamine, dicyclohexylamine, dibenzylamine, bis (trimethylsilyl) amine, morpholine, imidazole, indoline, indole, pyrrole, 2,5-dimethyl-pyrrole, 3,4-dimethyl-pyrrole, 3,4-dichloro-pyrrole, 2,3,4,5-tetrachloro-pyrrole, 2-acyl-pyrrole, pyrazole, pyrrolidine, or the like.

The amides used in the present invention may be metal amides derived from primary or secondary amines. For example, the amide may be produced by reacting the primary or secondary amine with a metal element selected from those belonging to the 1-, 2-, 4- and 13-Groups of the Periodic Table. Specific examples of the metal amides may include lithium amide, sodium ethyl-amide, calcium diethyl-amide, lithium diisopropyl-amide, potassium benzyl-amide, sodium bis-(trimethylsilyl) amide, lithium indolide, sodium pyrrolide, lithium pyrrolide, potassium pyrrolide, potassium pyrrolidide, aluminum-diethyl-pyrrolide, ethyl-aluminum-dipyrrolide, aluminum-tripyrrolide or the like.

Among these amines and amides, secondary amines, metal amides derived from secondary amines or a mixture thereof can be suitably used. Especially, examples of preferred secondary amines may include pyrrole, 2,5-dimethyl-pyrrole, 3,4-dimethyl-pyrrole, 3,4-dichloro-pyrrole, 2,3,4,5- tetrachloro-pyrrole and 2-acyl-pyrrole. Examples of preferred metal amides derived from secondary amines may include aluminum pyrrolide, ethyl-aluminum-dipyrrolide, aluminum-tripyrrolide, sodium pyrrolide, lithium pyrrolide and potassium pyrrolide. Among these pyrroles, the pyrrole derivatives having a hydrocarbon group bonded to a pyrrole ring are especially preferable.

Amides or imides other than those mentioned above, which are usable as the nitrogen-containing compound (b) in the present invention, includes the compounds of the following general formulae (1) to (3):

(1)

where $M^1$ is a hydrogen atom or a metal element selected from those belonging to the 1-, 2-, 11- and 13-Groups of periodic Table; $R^1$ is a hydrogen atom, a $C_1$–$C_{30}$ alkyl group, a $C_1$–$C_{30}$ alkenyl group, a $C_1$–$C_{30}$ aralkyl group, a $C_1$–$C_{30}$ substituted or unsubstituted aryl group which may contain not less than one hetero element; $R^2$ is a hydrogen atom, a $C_1$–$C_{30}$ alkyl group, a $C_1$–$C_{30}$ alkenyl group, a $C_1$–$C_{30}$ aralkyl group, a $C_1$–$C_{30}$ substituted or unsubstituted aryl group which may contain not less than one hetero element, or a $C_1$–$C_{30}$ acyl group of the general formula: $C(=O)R^3$ where $R^3$ has the same definition as $R^1$, and $R^1$ and $R^3$ may be same or different; $R^1$ and $R^2$ may constitute a ring;

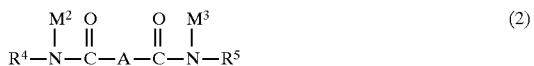
(2)

where $M^2$ and $M^3$ are independently a hydrogen atom or a metal element selected from those belonging to the 1-, 2-, 11- and 13-Groups of the Periodic Table; $R^4$ and $R^5$ are independently a hydrogen atom, a $C_1$–$C_{30}$ alkyl group, a $C_1$–$C_{30}$ alkenyl group, a $C_1$–$C_{30}$ aralkyl group, a $C_1$–$C_{30}$ substituted or unsubstituted aryl group which may contain not less than one hetero element; $R^4$ and $R^5$ may constitute a ring and A is an alkylene group which may contain not less than one unsaturated bond; and

(3)

where $M^4$ is a hydrogen atom or a metal element selected from those belonging to the 1-, 2-, 11- and 13-Groups of the Periodic Table; $R^6$ is a hydrogen atom, a $C_1$–$C_{30}$ alkyl group, a $C_1$–$C_{30}$ alkenyl group, a $C_1$–$C_{30}$ aralkyl group, a $C_1$–$C_{30}$ substituted or unsubstituted aryl group which may contain one or more hetero element; $R^7$ is a hydrogen atom, a $C_1$–$C_{30}$ alkyl group, a $C_1$–$C_{30}$ alkenyl group, a $C_1$–$C_{30}$ aralkyl group, a $C_1$–$C_{30}$ substituted or unsubstituted aryl group which may contain one or more hetero element, or a group of the general formula: $SO_2R^8$ where $R^8$ has the same definition as $R^6$, and $R^6$ and $R^8$ may be same or different; $R^6$ and $R^7$ may constitute a ring.

The amides represented by the general formula (1) or (2) may include, for example, acetamide, N-methyl-hexanamide, succinamide, maleamide, N-methyl-benzamide, imidazole-2-carbonamide, di-2-thenoyl-amine, β-lactam, δ-lactam, ε-caprolactam, and salts of these compounds with a metal selected from those belonging to the 1-, 2-, 11- and 13-Groups of the Periodic Table. The imides represented by the general formula (1) or (2) may include, for example, 1,2-cyclohexane-dicarboximide, succinimide, phthalimide, maleimide, 2,4,6-piperidine-trione, perhydroazecyne-2,10-dione and salts of these compounds with a metal selected from those belonging to the 1-, 2-, 11- and 13-Groups of the Periodic Table.

The sulfonamides and the sulfonimides represented by the above general formula (3) may include, for example, benzene-sulfonamide, N-methyl-methane-sulfonamide, N-methyl-trifluoromethyl-sulfonamide, and salts of these compounds with a metal selected from those belonging to 1-, 2-, 11- and 13-Groups of the Periodic Table. Among these amides or imides represented by the general formulae (1) to (3), the compounds represented by the above general formula (1) are preferable. Among them, the imide compounds having such a chemical structure in which $R^2$ of the general formula (1) is an acyl group of the formula: $C(=O)R^3$ and $R^1$ and $R^2$ constitute a ring, are especially preferable.

The alkyl aluminum compounds (c) used in the present invention has a chemical structure represented by the following general formula (4):

(4)

where $R^9$ and $R^{10}$ represent a hydrocarbon group having generally 1 to 15 carbon atoms, preferably 1 to 8 carbon atoms and may be same or different; X represents a halogen atom; m is a number more than 0 and not more than 3; and each of t, p and q is a number not less than 0 and less than 3 with the limitation that a sum of m, n, t and q is equal to 3.

Examples of the afore-mentioned alkyl aluminum compounds may include trialkyl aluminum compounds represented by the below-mentioned general formula (5), halogenated alkyl aluminum compounds represented by the below-mentioned general formula (6), alkoxy aluminum compounds represented by the below-mentioned general formula (7), hydrogenated alkyl aluminum compounds represented by the below-mentioned general formula (8), or the like. In each of the formulae (5) to (8), $R^9$, X and $R^{10}$ have the same definition as mentioned above.

(5)

(6)

wherein m is a number not less than 1.5 and less than 3.

(7)

wherein m is a number more than 0 and less than 3, preferably a number not less than 1.5 and less than 3.

(8)

wherein m is a number more than 0 and less than 3, preferably a number not less than 1.5 and less than 3.

Specific examples of the afore-mentioned alkyl aluminum compounds may include trimethyl aluminum, triethyl aluminum, triisobutyl aluminum, diethyl-aluminum-monochloride, diethyl-aluminum-ethoxide, diethyl-aluminum-hydride or the like. Among them, trialkyl aluminum compounds are particularly preferable, because the use of this compound can reduce an amount of undesirable by-product polymer. These alkyl aluminum compounds may be used in the form of a mixture of 2 or more different compounds, for example, a mixture of trialkyl aluminum and halogenated alkyl aluminum can be suitably used.

The catalyst according to the present invention is formed from the afore-mentioned three components (a) to (c). However, it is preferred that the catalyst further contains a halogen-containing compound (d) as one of the catalytic components. As the halogen-containing compounds (d), any compounds containing one or more halogen atoms can be used. Among them, the following halogen-containing compounds (1) to (4) are preferable.

The halogen-containing compounds (1) are the compounds containing an element selected from those belonging to the 3-, 4-, 5-, 6-, 13-, 14- and 15-Groups of the Periodic Table. Specific examples of the afore-mentioned halogen-containing compound (1) may include scandium chloride, yttrium chloride, lanthanum chloride, titanium tetrachloride, zirconium tetrachloride, hafnium tetrachloride, molybdenum chloride, manganese chloride, boron trichloride, aluminum chloride, diethyl aluminum chloride, ethyl aluminum sesquichloride, gallium chloride, carbon tetrachloride, chloroform, methylene chloride, dichloroethane, hexachlorobenzene, 1,3,5-trichlorobenzene, trityl chloride, silane tetrachloride, trimethyl-chlorosilane, germanium tetrachloride, tin tetrachloride, tributyl-tin chloride, phosphorus trichloride, antimony trichloride, trityl-hexachloro-antimonate, antimony pentachloride, bismuth trichloride, boron tribromide, aluminum tribromide, carbon tetrabromide, bromoform, bromobenzene, iodomethane, silicon tetrabromide, hexafluorobenzene, aluminum fluoride, or the like. Among these halogen-containing compounds (1), the compounds which are large in number of halogen atoms contained and soluble in an oligomerization solvent are preferred. As halogen atoms contained in the halogen-containing compounds, bromine or chlorine is suitable. When a high catalytic activity, a high selectivity for the aimed product and the like are totally evaluated, chlorine is more preferably. Examples of especially preferred halogen-containing compounds (1) may include carbon tetrachloride, chloroform, dichloroethane, titanium tetrachloride, germanium tetrachloride or tin tetrachloride. These halogen-containing compounds (1) may be used in the form of a mixture of 2 or more different compounds.

The halogen-containing compounds (2) used in the present invention may be linear hydrocarbons containing not less than 3 halogen substituents and having not less than 2 carbon atoms. The suitable linear hydrocarbons are linear saturated hydrocarbons. Among them, linear saturated hydrocarbons having not less than 3 halogen substituents bonded to adjacent two carbon atoms are preferable. Particularly preferred halogenated linear hydrocarbons are those represented by the following general formulae (9), (10) and (11).

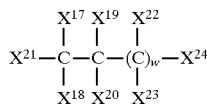
(9)

where $X_1$ to $X_8$ are independently a hydrogen atom or a halogen atom and at least three of $X_1$ to $X_5$ are halogen atoms, and r is an integer of 0 to 8.

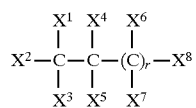
(10)

where $X^9$ to $X^{11}$ are independently a halogen atom; $X^{12}$ to $X^{16}$ are independently a halogen atom or a hydrogen atom, and s is an integer of 0 to 8.

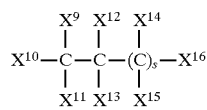
(11)

where $X^{17}$ to $X^{20}$ are independently a halogen atom; $X^{21}$ to $X^{24}$ are independently a halogen atom or a hydrogen atom; and w is an integer of 0 to 8.

Examples of the halogen atoms contained in the halogen-containing compounds (2) may include chlorine or bromine. Among them, when totally evaluated, chlorine is more preferable because it exhibits a high catalytic activity, a high selectivity for the aimed product and the like. Each of r, s and w of the general formulae (9) to (11) is preferably an integer of 0 to 3. Specific examples of the halogenated linear hydrocarbons represented by the general formulae (9) to (11) may include 1,1,1-trichloroethane, 1,1,2-trichloroethane, 1,1,2,2-tetrachloroethane, pentachloroethane, hexachloroethane, 1,1,1-trichloropropane, 1,1,2,2-tetrachloropropane, 1,1,1-trichlorobutane, 1,1,2,2-tetrachlorobutane, 1,1,1-tribromoethane, 1,1,2,2-tetrachloropentane, 1,1,1-tribromoethane, 1,1,2,2-tetrabromoethane, or the like. Among them, 1,1,1-trichloroethane, pentachloroethane, hexachloroethane, 1,1,2,2-tetrachloroethane are more preferable.

When the afore-mentioned halogen-containing compounds (2) is used, not only catalytic activity and trimer-selectivity are considerably improved but also a resistance to aged deterioration is enhanced.

The halogen-containing compounds (3) are halogenated cyclic hydrocarbons. As the cyclic hydrocarbons, cyclic saturated hydrocarbons are preferable. Especially preferred halogen-containing compounds (3) are cyclic saturated hydrocarbons having 3 halogen substituents. Examples of the halogen atoms contained in the halogen-containing compounds (3) may include chlorine or bromine. Among them, when a high catalytic activity, a high selectivity for the aimed product and the like are totally evaluated, chlorine is more preferable.

Specific examples of the halogen-containing compounds (3) may include tri-halogenated-cyclopropanes such as 1,2,3-trichloro-cyclopropane, 1,1,2-trichloro-cyclopropane, 1,2,3-tribromo-cyclopropane or 1,1,2-tribromo-cyclopropane, tetra-halogenated cyclopropane such as 1,1,2,3-tetrachloro-cyclopropane, 1,1,2,2-tetrachloro-cyclopropane, 1,1,2,3-tetrabromo-cyclobutane, or 1,1,2,2-tetrabromo-cyclopropane, penta-halogenated cyclopropanes such as pentachloro-cyclopropane or pentabromo-cyclopropane, hexa-halogenated cyclopropanes such as hexachloro-cyclopropane or hexabromo-cyclopropane, tri-halogenated cyclobutanes such as 1,2,3-trichloro-cyclobutane, 1,1,2-trichloro-cyclobutane, 1,2,3-tribromo-cyclobutane or 1,1,2-tribromo-cyclobutane, tetra-halogenated cyclobutanes such as 1,2,3,4-tetrachloro-cyclobutane, 1,1,2,3-tetrachloro-cyclobutane, 1,2,3,4-tetrabromo-cyclobutane or 1,1,2,3-tetrabromo-cyclobutane, penta-halogenated cyclobutanes such as 1,1,2,3,4-pentachloro-cyclobutane, 1,1,2,2,3-pentachloro-cyclobutane, 1,1,2,3,4-pentabromo-cyclobutane or 1,1,2,2,3-pentabromo-cyclobutane, hexa-halogenated cyclobutanes such as 1,1,2,2,3,4-hexachloro-cyclobutane, 1,1,2,2,3,3-hexachloro-cyclobutane, 1,1,2,2,3,4-hexabromo-cyclobutane or 1,1,2,2,3,3-hexabromo-cyclobutane, hepta-halogenated cyclobutanes such as heptachloro-cyclobutane or heptabromo-cyclobutane, octa-halogenated cyclobutanes such as octachloro-cyclobutane or octabromo-cyclobutane, or the like.

In addition, the specific examples of the halogen-containing compounds (3) may include tri-halogenated-cyclopentanes such as 1,2,3-trichloro-cyclopentane, 1,1,2-trichloro-cyclopentane, 1,2,3-tribromo-cyclopentane or 1,1,2-tribromo-cyclopentane, tetra-halogenated cyclopentanes such as 1,2,3,4-tetrachloro-cyclopentane, 1,1,2,3-tetrachloro-cyclopentane, 1,2,3,4-tetrabromo-cyclopentane or 1,1,2,3-tetrabromo-cyclopentane, penta-halogenated cyclopentanes such as 1,2,3,4,5-pentachloro-cyclopentane, 1,1,2,3,4-pentachloro-cyclopentane, 1,1,2,2,3-pentachloro-cyclopentane, 1,2,3,4,5-pentabromo-cyclopentane, 1,1,2,3,4-pentabromo-cyclopentane or 1,1,2,2,3-pentabromo-cyclopentane, hexa-halogenated cyclopentanes such as 1,1,2,3,4,5-hexachloro-cyclopentane, or 1,1,2,3,4,5-hexabromo-cyclopentane, hepta-halogenated cyclopentanes such as 1,1,2,2,3,4,5-heptachloro-cyclopentane or 1,1,2,2,3,4,5-heptabromo-cyclopentane, octa-halogenated cyclopentanes such as 1,1,2,2,3,3,4,5-octachloro-cyclopentane or 1,1,2,2,3,3,4,5-octabromo-cyclopentane, nona-halogenated cyclopentanes such as nonachloro-cyclopentane, deca-halogenated cyclopentanes such as decachloro-cyclopentane, or the like.

The specific examples of the halogen-containing compounds (3) may further include tri-halogenated-cyclohexanes such as 1,2,3-trichloro-cyclohexane, 1,1,2-trichloro-cyclohexane, 1,2,3-tribromo-cyclohexane or 1,1,2-tribromo-cyclohexane, tetra-halogenated cyclohexanes such as 1,2,3,4-tetrachloro-cyclohexane, 1,1,2,3-tetrachloro-cyclohexane, 1,2,3,4-tetrabromo-cyclohexane or 1,1,2,3-tetrabromo-cyclohexane, penta-halogenated cyclohexanes such as 1,2,3,4,5-pentachloro-cyclohexane, 1,1,2,3,4-pentachloro-cyclohexane, 1,1,2,2,3-pentachloro-cyclohexane, 1,2,3,4,5-pentabromo-cyclohexane, 1,1,2,3,4-pentabromo-cyclohexane or 1,1,2,2,3-pentabromo-cyclohexane, hexa-halogenated cyclohexanes such as 1,2,3,4,5,6-hexachloro-cyclohexane or 1,2,3,4,5,6-hexabromo-cyclohexane, hepta-halogenated cyclohexanes such as 1,1,2,3,4,5,6-heptachloro-cyclohexane or 1,1,2,3,4,5,6-heptabromo-cyclohexane, octa-halogenated cyclohexanes such as 1,1,2,2,3,4,5,6-octachloro-cyclohexane or 1,1,2,2,3,4,5,6-octabromo-cyclohexane, nona-halogenated cyclohexanes such as 1,1,2,2,3,3,4,5,6-nonachloro-cyclohexane, deca-halogenated cyclohexanes such as 1,1,2,2,3,3,4,4,5,6-decacyhloro-cyclohexane, undeca-halogenated cyclohexanes such as undecachloro-cyclohexane, dodeca-halogenated cyclohexanes such as dodecachloro-cyclohexane, or the like.

Among these halogen-containing compounds (3), 1,2,3-trichloro-cyclopropane, pentachloro-cyclopropane, 1,2,3,4-tetrachloro-cyclobutane, 1,2,3,4,5-pentachloro-cyclopentane and 1,2,3,4,5,6-hexachloro-cyclohexane are especially preferred.

When the halogen-containing compounds (3) are used, not only the catalytic activity and the trimer-selectivity are considerably improved but also the resistance to aged deterioration is enhanced.

The halogen-containing compounds (4) are represented by the following formula (12):

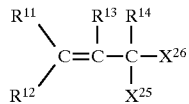

(12)

where $R^{11}$ to $R^{14}$ are independently a hydrogen atom or an alkyl group; $X^{25}$ is a hydrogen atom, an alkyl group or a halogen atom; and $X^{26}$ is a halogen atom.

Examples of the halogen atoms contained in the halogen-containing compounds (4) may include chlorine or bromine. Among them, when a high catalytic activity, a high selectivity for the aimed product and the like are totally evaluated, chlorine is more preferable. Specific examples of the halogen-containing compounds (4) may include allyl chloride, 3,3-dichloro-1-propene, 3-chloro-1-butene, 3,3-dichloro-1-butene, 1-chloro-2-butene, 1,1-dichloro-2-butene, 3-chloro-3-methyl-1-butene, 3-chloro-1-pentene, 3,3-dichloro-1-pentene, 4-chloro-2-pentene, 4,4-dichloro-2-pentene, 1-chloro-2-pentene, 1,1-dichloro-2-pentene, or the like. Among them, allyl chloride is most preferable.

When the halogen-containing compound (4) is used, not only the catalytic activity and the trimer-selectivity are considerably increased but also the amount of the halogen-containing compound can be reduced due to its high catalytic activity per a unit amount of the halogen atom. Further, since the amount of halogen-containing decomposition products generated in the course of reaction or distilling purification is small, there is an advantage that when the resultant trimer is subjected to distilling purification, the halogen-containing impurities is readily separated therefrom so that the aimed product having a high purity can be recovered.

Moreover, as the halogen-containing compounds, trifluoromethanesulfonic acid t-butyl-dimethylsilylester(t-BuMe$_2$SiOSO$_2$CF$_3$), tris (pentafluorophenyl)boron (B(C$_6$F$_5$)$_3$), trifluoromethane-sulfonic acid (CF$_3$SO$_3$H), hexafluoro-isopropanol ((CF$_3$)$_2$CHOH) or the like can be preferably used.

In accordance with the present invention, the oligomerization of α-olefin is carried out in a liquid reaction medium (reaction solvent) in the presence of the chromium-based catalyst which formed from the afore-mentioned catalytic components (a) to (c), preferably the catalytic components (a) to (d).

The α-olefins used as a raw material in the process of the present invention, may be substituted or unsubstituted α-olefins having 2 to 30 carbon atoms. Specific examples of the α-olefins may include ethylene, propylene, 1-butene, 1-hexene, 1-octene, 3-methyl-l-butene, 4-methyl-1-pentene, or the like. Among them, ethylene is preferable as the raw (α-olefin, because 1-hexene as a trimer thereof can be produced therefrom with a high yield and a high selectivity.

The reaction solvents used in the present invention may include aliphatic or alicyclic saturated hydrocarbons having 1 to 20 carbon atoms, such as butane, pentane, 3-methylpentane, hexane, heptane, 2-methylhexane, octane, cyclohexane, methylcyclohexane and decalin, and aromatic hydrocarbons such as benzene, toluene, xylene, ethyl benzene, mesitylene and tetralin, or the like. These solvents may be used singly or in the form of a mixture of not less than two different solvents In the process according to the present invention, the raw (α-olefins themselves or other α-olefins can be used as a solvent. It is preferred that α-olefin used as a solvent is kept in a liquid state at room temperature.

Especially, as the solvent, aliphatic or alicyclic saturated hydrocarbons having 4 to 7 carbon atoms is preferable. The use of such a solvent can prohibit the production of undesired by-product polymers. Further, when the alicyclic saturated hydrocarbon is used as the solvent, there is an advantage that a high catalytic activity can be obtained.

The catalyst used in the oligomerization of the present invention can be formed by mixing the chromium compound (a), the nitrogen-containing compound (b) selected from amines, amides and imides, and the alkyl aluminum compound (c), and optionally the halogen-containing compound (d) as an additional catalytic component, at a temperature of 20° to 200° C., preferably 50° to 150° C. The chromium-based catalyst may be previously prepared before the oligomerization reaction and thereafter the thus-prepared catalyst may be supplied to a reaction zone for the oligomerization. Alternatively, the respective catalytic components of the chromium-based catalyst may be supplied to the reaction zone and mixed together simultaneously with the oligomerization. Whichever method is used for the preparation of the chromium-based catalyst, it is preferred that the chromium compound (a) and the alkyl aluminum compound (c) are previously kept in non-contact with each other. That is, each of the chromium compound (a) and the alkyl aluminum compound (c) can be previously contacted with the nitrogen-containing compound (b) and the hydrogen-containing compound (d), but both the components (a) and (c) are preferably contacted with each other only after the α-olefin is supplied to the reaction zone.

The reason why the high-performance catalyst can be obtained under such a contact condition, is suggested such that the reaction product produced by the contact of the chromium compound (a) and the alkyl aluminum compound (c) is extremely unstable and therefore readily decomposed, while if the α-olefin is present in the reaction zone, the reaction product of the components (a) and (c) is rendered appropriately stable because the α-olefin is coordinated thereto.

Whichever method, i.e., the method of previously preparing the catalyst before the oligomerization or the method of forming the catalyst simultaneously with the oligomerization, is adopted, it is preferred that the α-olefin is present at a high concentration in the reaction solvent for forming the catalyst.

In the case where the formation of the catalyst is conducted in an atmosphere in which a low-boiling point α-olefin such as ethylene is present, the partial pressure of the low boiling point α-olefin is generally in the range about 3 to about 250 kg/cm$^2$. It is preferred that the formation of the catalyst is conducted in an atmosphere in which the partial pressure of the α-olefin is in the range of about 10 to about 200 kg/cm$^2$, especially about 20 to 100 kg/cm$^2$.

When the catalyst is formed in the afore-mentioned manner, there are advantages such as a considerably-high catalytic activity, a high selectivity for the trimer and an extremely-high purity of the resultant α-olefin oligomer.

Specifically, in the process according to the present invention, the respective catalytic components are contacted with each other by the below-mentioned methods (1) to (9). Incidentally, in the case where the previously-prepared catalyst is supplied to the reaction zone, the reaction solvent used for the preparation of the catalyst may be usually the same as those used in the oligomerization reaction but other solvents can also be used if required. In these methods, the α-olefin may be previously contained in the reaction solvent.

(1) A method in which the chromium compound (a) and the α-olefin are introduced into a solution containing the nitrogen-containing compound (b), the alkyl aluminum compound (c) and the halogen-containing compound (d);

(2) A method in which the alkyl aluminum compound (c) and the α-olefin are introduced into a solution containing the chromium compound (a), the halogen-containing compound (d) and the nitrogen-containing compound (b);

(3) A method in which the nitrogen-containing compound (b), the alkyl aluminum compound (c) and the α-olefin are introduced into a solution containing the chromium compound (a) and the halogen-containing compound (d);

(4) A method in which the chromium compound (a), the nitrogen-containing compound (b) and the α-olefin are introduced into a solution containing the alkyl aluminum compound (c) and the halogen-containing compound (d);

(5) A method in which the alkyl aluminum compound (c), the halogen-containing compound (d) and the α-olefin are introduced into a solution containing the chromium compound (a) and the nitrogen-containing compound (b);

(6) A method in which the chromium compound (a), the halogen-containing compound (d) and the α-olefin are introduced into a solution containing the nitrogen-containing compound (b) and the alkyl aluminum compound (c);

(7) A method in which the chromium compound (a), the nitrogen-containing compound (b), the halogen-containing compound (d) and the α-olefin are introduced into a solution containing the alkyl aluminum compound (c);

(8) A method in which the halogen-containing compound (d), the nitrogen-containing compound (b), the alkyl aluminum compound (c) and the α-olefin are introduced into a solution containing the chromium compound (a); and (9) A method in which the chromium compound (a), the nitrogen-containing compound (b), the alkyl aluminum compound (c), the halogen-containing compound (d) and α-olefin are simultaneously and independently introduced into the reaction solvent.

In the process according to the present invention, the catalyst may be previously prepared and then supplied to the reaction system as described above. It is preferred that the catalytic components (a) to (c) and further the catalytic component (d) are supplied to the reaction zone, and the chromium-based catalyst be formed in the reaction system simultaneously with the oligomerization reaction. Whichever method, i.e., the method of supplying the previously-prepared catalyst to the reaction system or the method of formed the catalyst simultaneously with the oligomerization, is adopted, the amount of the chromium compound (a) supplied is generally in the range of $1\times10^{-7}$ to 0.5 mol, preferably $5\times10^{-7}$ to 0.2 mol, more preferably $1\times10{-6}$ to $5\times10{-2}$ mol based on one liter of the reaction solvent. The amount of the nitrogen-containing compound (b) supplied is generally in the range of $1\times10^{-7}$ to 0.1 mol, preferably $5\times10^{-7}$ to $5\times10^{-2}$ mol , more preferably $1\times10^{-6}$ to $1\times10^{-2}$ mol based on one liter of the reaction solvent. The amount of the alkyl aluminum compound (c) supplied is generally in the range of $1\times10^{-7}$ to $7\times10^{-2}$ mol, preferably $5\times10^{-7}$ to $5\times10^{-2}$ mol, more preferably $1\times10^{-6}$ to $1\times10^{-2}$ mol based on one liter of the reaction solvent. The amount of the halogen-containing compound (d) supplied is generally in the range of $1\times10^{-7}$ to 0.1 mol, preferably $5\times10^{-7}$ to $5\times10^{-2}$ mol, more preferably $1\times10^{-6}$ to $1\times10^{-2}$ mol based on one liter of the reaction solvent.

Whichever method, i.e., the method of supplying the previously-prepared catalyst to the reaction system or the method of forming the catalyst simultaneously with the oligomerization, is adopted, the molar ratio between the catalytic components (a):(b):(c) is generally 1:0.1 to 100:0.1 to 500, preferably 1:0.1 to 10:1 to 100, more preferably 1:1 to 5:5 to 50. In the case where the halogen-containing compound (d) is used as an additional catalytic component, the molar ratio between the catalytic components (a):(b):(c):(d) is generally 1:0.1 to 100:0.1 to 500:0.1 to 100, preferably 1:0.1 to 10:1 to 100:0.1 to 20, more preferably 1:1 to 5:5 to 50:1 to 10. By using the catalyst having such a molar ratio, the α-olefin oligomer such as hexene can be produced from ethylene with a yield of not less than 90%. Further, in this case, the selectivity for 1-hexene can be enhanced to not less than 99%.

The oligomerization according to the present invention can be conducted by a continuous reaction method in which the raw α-olefin is continuously supplied to the reaction zone and the resultant oligomer is continuously discharged from the reaction zone.

When the oligomerization of α-olefin is continuously conducted by using the afore-mentioned catalyst, the molar ratio of α-olefin oligomer to the raw α-olefin in the reaction solution is maintained in the range of 0.05 to 1.00, preferably 0.10 to 0.80. The above-ranged molar ratio of the α-olefin oligomer to the raw, α-olefin can be achieved by controlling the amount of the catalyst supplied to the reactor or the reaction time (residence time). For example, when the amount of the catalyst supplied is decreased or the reaction time is shortened, the conversion of the α-olefin is decreased and in turn the amount of the α-olefin oligomer produced is reduced, so that the molar ratio of the α-olefin oligomer to the raw α-olefin in the reaction solution becomes decreased. Alternatively, the molar ratio can be decreased by increasing the amount of the raw α-olefin. The molar ratio of the α-olefin oligomer to the raw α-olefin in the reaction solution can be increased by reverse procedures to the above.

If the oligomerization of the α-olefin is conducted while adjusting the molar ratio of the α-olefin oligomer to the raw α-olefin to not more than 1.00, preferably 0.80, the production of the by-product having a higher boiling point than that of the aimed α-olefin oligomer is effectively prevented, so that the aimed α-olefin oligomer can be obtained with a high yield and a high selectivity.

However, when the molar ratio of the α-olefin oligomer to the raw α-olefin is decreased, the conversion of the α-olefin is also decreased. Accordingly, too small molar ratio of the α-olefin oligomer to the raw α-olefin is not advantageous unless there is a particular reason for doing so. For this reason, in accordance with the present invention, the molar ratio of the α-olefin oligomer to the raw α-olefin should be adjusted to not less than 0.05, preferably not less than 0.1 in view of both the prevention of the production of the by-products having a higher boiling point than that of the α-olefin, and efficiency in reaction operations.

Further, in accordance with the present invention, it is preferred that the concentration of the α-olefin in a liquid phase of the reaction zone is not less than 0.5 mol/liter. When the concentration of the α-olefin is less than 0.5 mol/liter, effective catalytically-active species for the oligomerization of the α-olefin cannot be formed, resulting in decrease in reaction rate of the oligomerization. This is disadvantageous for industrial use. On the other hand, when the concentration of the α-olefin is too high, the reaction pressure must be unnecessarily increased. This is also disadvantageous for industrial application of the process. Therefore, from a standpoint of the industrial application, it is more preferred that the concentration of the α-olefin in the liquid phase of the reaction zone is in the range of 1 to 7 mol/liter.

In addition, the residence time of the liquid phase portion in the reaction zone is preferably not more than 60 minutes. When the residence time of the liquid phase portion is more than 60 minutes, the catalyst is likely to suffer from aged deterioration and an inner olefin portion of 1-hexene is likely to be isomerized. Accordingly, it is preferred that the residence time for the liquid phase portion is in the range of 1 to 50 minutes.

In the process according to the present invention, the catalyst is continuously supplied to the reaction zone. At this time, it is preferred that the supplying rate of the catalyst to the reaction zone is controlled such that the concentration of chromium in the liquid phase of the reaction zone is not more than 1 ppm. If the concentration of chromium in the reaction zone is too high, there arises such a tendency that the catalytic activity of the catalyst and the selectivity for the α-olefin oligomer are deteriorated. On the other hand, if the concentration of chromium in the reaction zone is too low, the reaction rate is unpractically decreased. Accordingly, it is preferred that the concentration of chromium in the liquid phase of the reaction zone is controlled to the range of 0.01 to 1 ppm, especially 0.1 to 0.5 ppm. Incidentally, the afore-mentioned concentration of chromium, means a weight of metal chromium per a unit weight of the reaction solution in the reaction zone.

In accordance with the present invention, it is preferred that the reaction conditions for the oligomerization of the α-olefin meet the requirements of the following formulae (1) and (2):

$$T \geq 105° C. \tag{1}$$

$$P > 0.5T - 15 \tag{2}$$

where T represents a reaction temperature (°C.) and P represents a reaction pressure (kg/cm²G (Gauge pressure)).

In the prior art, it has been described that the reaction temperature of not more than 70° C. is preferable because the by-products produced in the reaction solution are granulated to facilitate the separation of solid and liquid from each other. In Japanese Patent Application Laid-Open (KOKAI) No. 8-3216, as a general description, there are description for the reaction temperature ranging of 0° to 250° C. and the reaction pressure of a normal pressure to 250 kg/cm². In Examples of the above mentioned Japanese Patent Application, the reaction is conducted at the reaction temperature of 80° C. and the reaction pressure of 35 kg/cm².

On the other hand, in the process according to the present invention, it is required to adopt a reaction temperature of at least 105° C. and a reaction pressure of at least 37.5 kg/cm²G when the reaction temperature is 105° C. In accordance with the present invention, by adjusting the reaction temperature to not less than 105° C., preferably 120° to 150° C., the by-product polymers can be present in a dissolved state in the reaction solution. As a result, there do not arise problems such as adhesion of the by-product polymers to an inner wall of the reactor or the like. Further, such a reaction solution dissolving the by-product polymers can be readily subjected to a method in which the by-product polymers are concentrated together with the catalytic components while being prevented from depositing in the reactor, and then both are separated from each other. In addition, in accordance with the present invention, the reaction temperature can be increased while keeping the constant relationship with the reaction pressure, so that the performance of the chromium-based catalyst is not deteriorated and a high catalytic activity of the catalyst can be maintained. Incidentally, the residence time of the reaction solution in the reaction zone is not more than 1 hour, preferably in the range of 1 to 50 minutes.

In the case where the method of conducting the formation of the chromium catalyst and the oligomerization of the α-olefin simultaneously, is adopted, it is preferred that the catalytic components of the chromium catalyst and the α-olefin is supplied to initiate the oligomerization reaction such that the respective molar ratios of the nitrogen-containing compound (b), the alkyl aluminum compound (c) and the halogen-containing compound (d) to the chromium compound (a) at the initiation of the reaction becomes larger than those in a steady state.

Incidentally, the wording "at the initiation of the reaction" means a time when the chromium compound (a) is first brought into contact with the nitrogen-containing compound (b), the alkyl aluminum compound (c) and the halogen-containing compound (d) to initiate the oligomerization reaction of the α-olefin.

In accordance with the present invention, the catalytic components of the chromium-based catalyst are supplied to the reaction zone under the afore-mentioned conditions. In consequence, the chromium-based catalyst having a high catalytic activity can be obtained without necessity of an induction period for imparting a high catalytic activity to the catalyst at an initial stage of the reaction. Further, the oligomerization of the α-olefin can be conducted with a high catalytic activity of the catalyst while considerably preventing the production of the by-product polymers. The reason therefor is not sufficiently apparent but is suggested as follows. In the case where the catalytic components of the chromium catalyst and the α-olefin are supplied to the reaction zone such that the respective molar ratios of the nitrogen-containing compound (b), the alkyl aluminum compound (c) and the halogen-containing compound (d) to the chromium compound (a) at the initiation of the reaction becomes larger than those in a steady state, catalytically-active species effective for the oligomerization of α-olefin can be formed effectively.

The concentration of the chromium compound (a) in the reaction zone at the initiation of the oligomerization reaction is preferably not more than $2 \times 10^{-2}$ millimoles, more preferably in the range of $5 \times 10^{-7}$ to $1 \times 10^{-2}$ millimoles based on one liter of the reaction solvent. The molar ratio between the catalytic components (a):(b):(c):(d) in the reaction zone is preferably 1: not less than 150: not less than 1500: not less than 150, more preferably 1:150 to 1000:1500 to 5000:150 to 1000, still more preferably 1:200 to 500:200 to 3000:200 to 500.

When the molar ratio of the catalytic components (b), (c) and (d) to the catalytic component (a) at the initial stage of the reaction is too low, there is a tendency that the catalyst exhibits a low catalytic activity and the amount of the by-product polymers produced is increased.

By controlling the molar ratios of the respective catalytic components to the afore-mentioned ranges, the catalytic activity of the catalyst can be considerably enhanced at the initial stage of the reaction and the oligomerization of α-olefin can be performed while maintaining the high catalytic activity. Further, the amount of the by-product polymers produced can be limited to a considerably low level. The reason therefor is not sufficiently apparent but is suggested as follows. When the molar ratios of the catalytic components (b), (c) and (d) to the catalytic component (a) at the initial stage of the reaction is too low, effective catalytically-active species for the oligomerization of α-olefin cannot be formed but the catalytically-active components effective for the production of the by-product polymers are rather formed. On the other hand, in the case where the molar ratio lies within the afore-mentioned ranges, the effective catalytically-active components for the oligomerization of α-olefin can be extremely readily produced.

The oligomerization of α-olefin according to the present invention can be conducted at a reaction temperature ranging generally from 20° C. to 200° C., preferably from 50° C. to 150° C., under a reaction pressure ranging from 10 to 200 kg/cm$^2$, preferably from 20 to 100 kg/cm$^2$. In addition, the coexistence of the hydrogen in the reaction zone provides further advantages such as the increase in catalytic activity and selectivity for the trimer and the decrease in amount of the polymers adhered to an inner wall of the reactor. The amount of the coexisting hydrogen in a gas phase of the reaction zone is preferably in the range of 0.1 to 15% by volume.

The oligomerization of α-olefin according to the present invention can be conducted by using various reactors. The reactors usable for conducting the process according to the present invention include, for example, a gas-stripping-type reactor, a loop-type reactor, a continuous stirring tank reactor, a gas-bubble column-type reactor, tubular reactor or the like.

In the case where the gas-stripping type reactor is used, an ethylene gas is continuously fed into the vessel-shaped reactor, thereby causing the trimerization of ethylene in a reaction solvent having a boiling point higher than that of 1-hexene in the presence of the chromium-based catalyst under heated and pressurized conditions. The resultant 1-hexene in a gas phase of the reactor is continuously discharged together with an unreacted ethylene gas from the rector and then the ethylene gas is separated from the discharged gas to recover 1-hexene.

In the case where the loop-type reactor used, the oligomerization of α-olefin is conducted while circulating a reaction solution containing the α-olefin and the chromium-based catalyst through a circular flow path of the reactor. This type reactor can prevent the by-product polymers from being adhered to a cooled wall thereof and maintain a high heat-removing efficiency.

Among them, the continuous stirring tank reactor is especially preferred.

The continuous stirring tank reactor usable in the present invention has such a structure in which partitions are disposed at a distance on an outer surface of an inner cylinder perpendicularly thereto, and an outer strip is spanned between the tip ends of the partitions, thereby forming a wall structure (hereinafter referred to merely as "temperature-controlling element") having a flow path for a heating medium between the inner cylinder, the outer strip and the partitions, and the temperature-controlling element is fixed within a container such that the outer strip thereof faces an inner wall of the container; or another structure in which the temperature-controlling element is fixed within a container such that the outer strips thereof face an inner wall of the container in a spaced relation, and the space of the lower and upper portions between the outer strip of the temperature-controlling element and the inner surface of the container is sealed so as to form a sealed chamber.

By using continuous stirring tank reactors having such structures, a wall thickness of portions for separating a content of the reactor from the cooling medium can be thin, so that the heat of reaction can be effectively removed. Further, since welded portions occupies only a small area on an inner surface of the reactor, the oligomerization of α-olefin can be performed in a continuous and stable manner for a long period of time without adhesion of the by-product polymers thereto.

The α-olefin oligomer can be recovered from the liquid reaction product in the reactor by an ordinary method. In accordance with the present invention, after the oligomerization of α-olefin is conducted in the reactor in the presence of the chromium-based catalyst and the reaction solvent, a part or a whole of the resultant reaction solution is fed into a degassing tower where unreacted α-olefin is recovered.

Next, the reaction solution treated in the degassing tower is fed into a product-distilling tower where the resultant α-olefin oligomer can be recovered in the form of a distillate.

At this time, it is preferred that in a process line from an outlet of the reactor to an inlet of the product-distilling tower, the reaction solution is maintained at a temperature of 100° to 150° C., and the residence time of the reaction solution from the supply to the degassing tower to the supply to the product-distilling tower is not more than 1 hour.

When the reaction temperature is maintained at less than 100° C., there arises various troubles due to the adhesion or deposition of the by-product polymers in the process line, for example, equipment such as feed conduits. On the other hand, when the reaction temperature is more than 150° C., the aimed product is subjected to isomerization so that the yield of the aimed α-olefin oligomer recovered from the product distilling tower is decreased. Even if the reaction temperature is not more than 150° C., when the residence time of the reaction solution from the supply to the degassing tower to the supply to the product-distilling tower is more than one hour, the isomerization of the reaction product cannot be sufficiently prevented. The residence time of the reaction solution is suitably decreased as the reaction temperature to be maintained is increased. It is especially preferred that the residence time be not more than 30 minutes.

In accordance with the present invention, the separation of the by-product polymers is preferably conducted after being concentrated together with the catalytic components. Such a separating method enables the catalytic components to be extremely readily separated from the by-product polymers because of a high plasticity of the by-product polymers. Therefore, the use of a solid-liquid separating apparatus can be omitted for the removal of the by-product polymers, thereby rendering the process compact.

According to the afore-mentioned preferred embodiments of the present invention, losses of both the by-product polymers and the catalytic components up to simultaneous recovering process thereof are limited to a minimum level.

In accordance with the present invention, the concentration and separation process of the by-product polymers and catalytic components can also be performed simultaneously with removal of a whole components having low boiling points by simple distillation from the reaction solution. Further, the separation of the by-product polymers and the catalytic components can be conducted simultaneously with a final stage of the separation process in which the respective components are in turn separated by distillation from the degassed reaction solution.

For example, in the case where ethylene is used as the α-olefin, 1-hexene can be obtained as the aimed α-olefin oligomer. In this case, de-ethylene treatment is conducted after the reaction. Next, 1-hexene and the reaction solvent are removed by distillation from the reaction solution, and the catalytic components and polyethylene as the by-product polymer are concentrated together and separated from the reaction solution. The resultant concentrated solution containing the by-product polymer and the catalytic components as it is can be discharged for disposal thereof.

EXAMPLES

The present invention is described in more detail below by way of examples and comparative examples. However, these examples are not intended to limit the scope of the present invention.

Example 1

Two liter-autoclave equipped with a stirrer, two feed pipes for a catalyst and a discharge pipe for removal of a reaction solution was heated and dried at 150° C. in a dryer, and assembled. The content of the autoclave was vacuum-evacuated and replaced with a nitrogen gas.

An n-heptane solution of 2,5-dimethyl-pyrrole, an n-heptane solution of triethyl aluminum and an n-heptane solution of carbon tetrachloride were continuously charged at feed rates of 0.031 mmol (millimole)/hr, 0.16 mmol/hr and 0.021 mmol/hr, respectively, into the thus-assembled autoclave through one of the feed pipes. On the other hand, ethylene and an n-heptane solution of chromium (III)-2-ethyl-hexanoate was continuously introduced at a feed rate of 0.010 mmol/hr (5.0 mg/hr) into the autoclave through the other of the feed pipes. The total feed rate of n-heptane charged was one liter/hr. While maintaining the temperature of the autoclave at 80° C., ethylene was continuously fed into the autoclave so as to keep the total pressure of ethylene in the autoclave at 35 $kg/cm^2G$ to conduct a oligomerization thereof. The resultant reaction solution was removed from the autoclave through the discharge pipe such that the liquid content in the autoclave was 1 liter. The discharged reaction solution was introduced into a degassing tank where the reaction solution is degassed up to a normal pressure. Thereafter, the liquid component and the gas component were analyzed by gas-chromatography. The results are shown in Table 1.

Examples 2 to 18 and
Comparative Examples 1 to 3

The same procedures as defined in Example 1 were conducted except that the reaction conditions were changed as shown in Table 1. In Example 18, chromium (III)-acetyl-acetonate was used as chromium compound in place of chromium (III)-2-ethyl-hexanoate. The results are also shown in Table 1.

TABLE 1

| Example No. | Example 1 | Example 2 | Example 3 |
|---|---|---|---|
| Flow rate of solvent (l/hr) | 1 | 1 | 1 |
| Rate of Cr compound feed (mg/hr) | 5 | 10 | 10 |
| Cr compound (mmol/hr) | 0.010 | 0.021 | 0.021 |
| 2,5-DMP (mmol/hr) | 0.031 | 0.062 | 0.062 |
| Triethyl aluminum (mmol/hr) | 0.16 | 0.31 | 0.31 |
| Sort of halogen-containing compound | Carbon tetrachloride | Carbon tetrachloride | Carbon tetrachloride |
| Halogen-containing compound (mmol/hr) | 0.021 | 0.042 | 0.042 |
| Molar ratio of catalytic components (a:b:c:d) | 1:3:15:2 | 1:3:15:2 | 1:3:15:2 |
| Reaction pressure (KG)* | 35 | 35 | 50 |
| Reaction temperature (°C.) | 80 | 80 | 80 |
| Residence time (hr) | 0.64 | 0.49 | 0.54 |
| Amount of product (g/hr) | 102 | 323 | 486 |
| Cr concentration in reaction zone (ppm) | 0.58 | 0.89 | 0.74 |
| Ethylene concentration in reaction zone (mol/l) | 2.76 | 2.76 | 4.09 |
| Molar ratio of 1-hexene to ethylene | 0.27 | 0.65 | 0.6 |
| Composition distribution (wt %) | | | |
| Whole of C6 | 97 | 95.2 | 95.3 |
| Content of 1-hexene in C6 | 99.7 | 99.8 | 99.7 |
| By-product polyethylene | 0.025 | 0.016 | 0.017 |
| Catalytic efficiency | $1.88 \times 10^5$ | $2.99 \times 10^5$ | $4.50 \times 10^5$ |

TABLE 1-continued

| Example No. | Example 4 | Example 5 | Example 6 |
|---|---|---|---|
| Flow rate of solvent (l/hr) | 1.8 | 1.8 | 4 |
| Rate of Cr compound feed (mg/hr) | 5.4 | 5.4 | 12 |
| Cr compound (mmol/hr) | 0.011 | 0.011 | 0.025 |
| 2,5-DMP (mmol/hr) | 0.067 | 0.067 | 0.149 |
| Triethyl aluminum (mmol/hr) | 0.45 | 0.45 | 1.00 |
| Sort of halogen-containing compound | Hexachloro-ethane | Hexachloro-ethane | Hexachloro-ethane |
| Halogen-containing compound (mmol/hr) | 0.045 | 0.045 | 0.100 |
| Molar ratio of catalytic components (a:b:c:d) | 1:6:40:4 | 1:6:40:4 | 1:6:40:4 |
| Reaction pressure (KG)* | 35 | 50 | 50 |
| Reaction temperature (°C.) | 80 | 105 | 105 |
| Residence time (hr) | 0.29 | 0.25 | 0.12 |
| Amount of product (g/hr) | 459 | 551 | 838 |
| Cr concentration in reaction zone (ppm) | 0.29 | 0.26 | 0.29 |
| Ethylene concentration in reaction zone (mol/l) | 2.75 | 3.23 | 3.23 |
| Molar ratio of 1-hexene to ethylene | 0.55 | 0.48 | 0.37 |
| Composition distribution (wt %) | | | |
| Whole of C6 | 95.1 | 95.9 | 96.8 |
| Content of 1-hexene in C6 | 99.6 | 99.5 | 99.5 |
| By-product polyethylene | 0.1 | 0.035 | 0.023 |
| Catalytic efficiency | $7.45 \times 10^5$ | $9.45 \times 10^5$ | $6.47 \times 10^5$ |

| Example No. | Example 7 | Example 8 | Example 9 |
|---|---|---|---|
| Flow rate of solvent (l/hr) | 1.8 | 4 | 4 |
| Rate of Cr compound feed (mg/hr) | 5.4 | 12 | 12 |
| Cr compound (mmol/hr) | 0.011 | 0.025 | 0.025 |
| 2,5-DMP (mmol/hr) | 0.067 | 0.149 | 0.149 |
| Triethyl aluminum (mmol/hr) | 0.45 | 1.00 | 1.00 |
| Sort of halogen-containing compound | Hexachloro-ethane | Hexachloro-ethane | Hexachloro-ethane |
| Halogen-containing compound (mmol/hr) | 0.045 | 0.100 | 0.100 |
| Molar ratio of catalytic components (a:b:c:d) | 1:6:40:4 | 1:6:40:4 | 1:6:40:4 |
| Reaction pressure (KG)* | 70 | 70 | 35 |
| Reaction temperature (°C.) | 105 | 105 | 120 |
| Residence time (hr) | 0.17 | 0.1 | 0.18 |
| Amount of product (g/hr) | 907 | 1129 | 77 |
| Cr concentration in reaction zone (ppm) | 0.19 | 0.24 | 0.4 |
| Ethylene concentration in reaction zone (mol/l) | 4.62 | 4.21 | 1.84 |
| Molar ratio of 1-hexene to ethylene | 0.38 | 0.29 | 0.09 |
| Composition distribution (wt %) | | | |
| Whole of C6 | 95.8 | 96.5 | 97.6 |
| Content of 1-hexene in C6 | 99.6 | 99.6 | 97.2 |
| By-product polyethylene | 0.064 | 0.051 | 0.441 |
| Catalytic efficiency | $1.55 \times 10^6$ | $8.71 \times 10^5$ | $5.93 \times 10^4$ |

| Example No. | Example 10 | Example 11 | Example 12 |
|---|---|---|---|
| Flow rate of solvent (l/hr) | 1.8 | 4 | 1.8 |
| Rate of Cr compound feed (mg/hr) | 5.4 | 12 | 5.4 |
| Cr compound (mmol/hr) | 0.011 | 0.025 | 0.011 |
| 2,5-DMP (mmol/hr) | 0.067 | 0.149 | 0.067 |
| Triethyl aluminum (mmol/hr) | 0.45 | 1.00 | 0.45 |
| Sort of halogen-containing compound | Hexachloro-ethane | Hexachloro-ethane | Hexachloro-ethane |
| Halogen-containing compound (mmol/hr) | 0.045 | 0.100 | 0.045 |
| Molar ratio of catalytic components (a:b:c:d) | 1:6:40:4 | 1:6:40:4 | 1:6:40:4 |
| Reaction pressure (KG)* | 50 | 50 | 70 |
| Reaction temperature (°C.) | 120 | 120 | 120 |
| Residence time (hr) | 0.28 | 0.14 | 0.2 |
| Amount of product (g/hr) | 385 | 523 | 653 |
| Cr concentration in reaction zone (ppm) | 0.3 | 0.33 | 0.23 |
| Ethylene concentration in reaction zone (mol/l) | 2.7 | 2.7 | 3.88 |
| Molar ratio of 1-hexene to ethylene | 0.45 | 0.3 | 0.38 |
| Composition distribution (wt %) | | | |
| Whole of C6 | 95.5 | 96.7 | 95.4 |
| Content of 1-hexene in C6 | 99.5 | 99.5 | 99.5 |
| By-product polyethylene | 0.045 | 0.026 | 0.134 |
| Catalytic efficiency | $6.60 \times 10^5$ | $4.04 \times 10^5$ | $1.12 \times 10^6$ |

| Example No. | Example 13 | Example 14 | Example 15 |
|---|---|---|---|
| Flow rate of solvent (l/hr) | 4 | 1.8 | 4 |
| Rate of Cr compound feed (mg/hr) | 12 | 5.4 | 12 |
| Cr compound (mmol/hr) | 0.025 | 0.011 | 0.025 |
| 2,5-DMP (mmol/hr) | 0.149 | 0.067 | 0.149 |
| Triethyl aluminum (mmol/hr) | 1.00 | 0.45 | 1.00 |
| Sort of halogen-containing compound | Hexachloro-ethane | Hexachloro-ethane | Hexachloro-ethane |
| Halogen-containing compound (mmol/hr) | 0.100 | 0.045 | 0.100 |
| Molar ratio of catalytic components (a:b:c:d) | 1:6:40:4 | 1:6:40:4 | 1:6:40:4 |
| Reaction pressure (KG)* | 70 | 50 | 50 |
| Reaction temperature (°C.) | 120 | 140 | 140 |
| Residence time (hr) | 0.1 | 0.3 | 0.14 |
| Amount of product (g/hr) | 986 | 209 | 387 |
| Cr concentration in reaction zone (ppm) | 0.26 | 0.34 | 0.35 |
| Ethylene concentration in reaction zone (mol/l) | 3.88 | 2.29 | 2.29 |
| Molar ratio of 1-hexene to ethylene | 0.29 | 0.32 | 0.28 |
| Composition distribution (wt %) | | | |
| Whole of C6 | 96.6 | 95.1 | 96.7 |
| Content of 1-hexene in C6 | 99.5 | 98.9 | 99.1 |
| By-product polyethylene | 0.03 | 0.305 | 0.059 |
| Catalytic efficiency | $7.61 \times 10^5$ | $3.59 \times 10^5$ | $3.06 \times 10^5$ |

| Example No. | Example 16 | Example 17 | Example 18 |
|---|---|---|---|
| Flow rate of solvent (l/hr) | 1.8 | 4 | 1.8 |
| Rate of Cr compound feed (mg/hr) | 5.4 | 12 | 3.96 |
| Cr compound (mmol/hr) | 0.011 | 0.025 | 0.011 |
| 2,5-DMP (mmol/hr) | 0.067 | 0.149 | 0.067 |
| Triethyl aluminum (mmol/hr) | 0.45 | 1.00 | 0.45 |
| Sort of halogen-containing compound | Hexachloro-ethane | Hexachloro-ethane | Hexachloro-ethane |
| Halogen-containing compound (mmol/hr) | 0.045 | 0.100 | 0.045 |
| Molar ratio of catalytic components (a:b:c:d) | 1:6:40:4 | 1:6:40:4 | 1:6:40:4 |
| Reaction pressure (KG)* | 70 | 70 | 50 |
| Reaction temperature (°C.) | 140 | 140 | 120 |
| Residence time (hr) | 0.23 | 0.11 | 0.27 |
| Amount of product (g/hr) | 391 | 702 | 91.2 |
| Cr concentration in reaction zone (ppm) | 0.28 | 0.29 | 0.29 |
| Ethylene concentration in reaction zone (mol/l) | 3.29 | 3.29 | 2.7 |
| Molar ratio of 1-hexene to ethylene | 0.31 | 0.26 | 0.44 |
| Composition distribution (wt %) | | | |
| Whole of C6 | 95.3 | 96.3 | 93.9 |
| Content of 1-hexene in C6 | 99.1 | 99.2 | 99.3 |

TABLE 1-continued

| | | | |
|---|---|---|---|
| By-product polyethylene | 0.163 | 0.065 | 0.22 |
| Catalytic efficiency | $6.70 \times 10^5$ | $5.41 \times 10^5$ | $6.11 \times 10^5$ |

| Example No. | Comparative Example 1 | Comparative Example 2 | Comparative Example 3 |
|---|---|---|---|
| Flow rate of solvent (l/hr) | 1 | 4 | 1 |
| Rate of Cr compound feed (mg/hr) | 60 | 12 | 100 |
| Cr compound (mmol/hr) | 0.130 | 0.025 | 0.208 |
| 2,5-DMP (mmol/hr) | 0.370 | 0.149 | 0.623 |
| Triethyl aluminum (mmol/hr) | 1.90 | 1.00 | 3.11 |
| Sort of halogen-containing compound | Carbon tetra-chloride | Hexachloro-ethane | Carbon tetra-chloride |
| Halogen-containing compound (mmol/hr) | 0.260 | 0.100 | 0.415 |
| Molar ratio of catalytic components (a:b:c:d) | 1:3:15:2 | 1:6:40:4 | 1:3:15:2 |
| Reaction pressure (KG)* | 35 | 35 | 35 |
| Reaction temperature (°C.) | 80 | 140 | 80 |
| Residence time (hr) | 0.36 | 0.17 | 0.21 |
| Amount of product (g/hr) | 1210 | 33 | 1640 |
| Cr concentration in reaction zone (ppm) | 2.86 | 0.42 | 4 |
| Ethylene concentration in reaction zone (mol/l) | 2.76 | 1.55 | 2.76 |
| Molar ratio of 1-hexene to ethylene | 1.26 | 0.04 | 1.38 |
| Composition distribution (wt %) | | | |
| Whole of C6 | 90.7 | 94.3 | 91.9 |
| Content of 1-hexene in C6 | 99.5 | 95.1 | 99.5 |
| By-product polyethylene | 0.05 | 1.03 | 0.07 |
| Catalytic efficiency | $1.68 \times 10^5$ | $2.53 \times 10^4$ | $1.52 \times 10^5$ |

*KG means "kg/cm$^2$G (Gauge pressure)".

As seen from Table 1, the processes of Examples according to the present invention in which the molar ratios of 1-hexene to ethylene in the reaction solution were in the range of 0.05 to 1.00, could be conducted with a higher selectivity for a whole C6 hydrocarbons and a higher catalytic efficiency as compared with those of Comparative Examples 1 and 2.

The comparisons between Example 9 and Examples 10 to 13 and 18 (in the case of the reaction temperature of 120° C.), and between Examples 14 and 15 and Examples 16 and 17 (in the case of the reaction temperature of 140° C.) reveal that by adjusting the reaction pressure to the particular range (P kg/cm$^2$G>0.5T−15), the chromium-based catalyst could maintain a high catalytic efficiency without deterioration in performance thereof even when the reaction temperature T (°C.) was maintained at a relatively high value.

Example 19

The continuous oligomerization of ethylene was conducted by the process using apparatuses comprising a complete continuous stirring tank reactor, a degassing tank, a product-distilling tower equipped with two side stream discharge pipes and having total 30 distilling stages, and an evaporator. The apparatuses further comprises a compressor disposed between the reactor and the degassing tank to circulate the degassed ethylene to the reactor. Incidentally, a 20 liter-autoclave equipped with two feed pipes was used as the continuous stirring tank reactor. Further, as the evaporator, there was used a monotube-type evaporator (Tradename: "CRUX SYSTEM" manufactured by HOSOKAWA-MIKARON Co., Ltd.) equipped with a heating tube having a length of 8 m and a pressure-reducible collecting can.

Ethylene, an n-heptane solution of chromium (III) 2-ethyl-hexanoate (a) and an n-heptane solution of hexachloroethane (d) were continuously introduced into the continuous stirring tank reactor through one of the feed pipes thereof. Simultaneously, an n-heptane solution of 2,5-dimethyl-pyrrole (b) and an n-heptane solution of triethyl aluminum (c) were continuously charged into the reactor through the other of the feed pipes thereof. The molar ratio between the respective components (a):(b):(c):(d) was adjusted to 1:6:40:4. The reaction was conducted at 120° C. and 50 kg/cm$^2$G.

The reaction solution was continuously removed from the reactor and the removed reaction solution was fed into the degassing tank while maintaining the solution at 120° C. While being maintained substantially at 120° C., the degassed reaction solution was then fed into the product-distilling tower. A portion of the reaction solution from the bottom of the product-distilling tower was fed to the evaporator and concentrated. The n-heptane solvent and the resultant hexene product were removed as a side-cut from the 8th-stage and 26th-stage side-stream pipes, respectively, and recovered from the bottom of the tower. Further, components having lower boiling points than that of hexene were distilled and recovered from a top of the tower.

High-boiling components gasified in the evaporator were condensed and recovered. Polyethylene as a by-product polymer was concentrated together with the catalytic components and recovered from the lower portion of the collecting chamber. On the other hand, ethylene degassed in the degassing tank was fed into the compressor and then the pressurized ethylene was circulated to the reactor. Also, the n-heptane recovered from the product-distilling tower was circulated to the reactor through a circulating pipe. Operational conditions of respective units disposed on the product-distilling tower are shown in Table 2. In addition, the mass balance in the afore-mentioned processes are shown in Table 3. Incidentally, "Cr(2EHA)$_3$" in Table 3 represents chromium (III) 2-ethyl-hexanoate.

TABLE 2

| | |
|---|---|
| Product-distilling tower | Pressure at top of tower: 3 kg/cm$^2$G |
| | Reflux ratio (R/D): 18 |
| | Tower bottom temperature: 162° C. |
| Temperature of heating pipe | 200° C. |
| Temperature of collecting can | 150° C. |
| Pressure of collecting can | 200 Torr |

TABLE 3

| | Reaction solution | Degassed solution | Solution from bottom of distilling tower |
|---|---|---|---|
| unit: /hr | 42.0 kg | 35.9 kg | 0.28 kg |
| Cr(2EHA)$_3$ (ppm) | 3.0 | 3.5 | 134 |
| 2,5-dimethyl-pyrrole (ppm) | 3.6 | 4.2 | 159 |
| Triethyl aluminum (ppm) | 28.4 | 33.0 | 1271 |
| Hexachloro-ethane (ppm) | 7.4 | 8.6 | 329 |
| Heptane (wt %) | 64.7 | 75.8 | 0.0 |
| Ethylene (wt %) | 14.6 | 0.0 | 0.0 |
| C6 components (wt %) | 20.0 | 23.4 | 0.0 |
| High-boiling components (wt %) | 0.60 | 0.70 | 89.4 |
| Polyethylene (ppm) | 700 | 820 | 10.43 wt % |
| Total | 100.0 | 100.0 | 100.0 |

TABLE 3-continued

|  | Evaporated component from evaporator | Concentrated component from evaporator |
|---|---|---|
| unit: /hr | 0.25 kg | 29.8 g |
| Cr(2EHA)$_3$ (ppm) | 0.0 | 0.127 wt % |
| 2,5-dimethyl-pyrrole (ppm) | 177.7 | 0.0 |
| Triethyl aluminum (ppm) | 0.0 | 1.20 wt % |
| Hexachloro-ethane (ppm) | 368.4 | 0.0 |
| Heptane (wt %) | 0.0 | 0.0 |
| Ethylene (wt %) | 0.0 | 0.0 |
| C6 components (wt %) | 0.0 | 0.0 |
| High-boiling components (wt %) | 99.9 | 0.0 |
| Polyethylene (ppm) | 0.0 | 98.7 wt % |
| Total | 100.0 | 100.0 |

Note:
Content of 1-hexene in C6 components: 99.5% by weight, Molar ratio of 1-hexene to ethylene: 0.45, Catalytic efficiency: 614,198 g-1-hexene/g-chromium In the operation of the evaporator in the afore-mentioned process, the metal-containing catalytic components were concentrated together with polyethylene as a by-product and recovered in the form of a mixture thereof. The polyethylene recovered was dropped by its own weight from the bottom of the collecting chamber because of the plasticity of the polyethylene. This indicated that the evaporator was operated in a good condition.

Example 20

The same procedure for continuous oligomerization of ethylene as defined in Example 19 was conducted except that tetrachloroethane was used as the halogen-containing compound. The mass balance in the afore-mentioned process are shown in Table 4. The evaporator was also operated in a good condition as in Example 19.

TABLE 4

|  | Reaction solution | Degassed solution | Solution from bottom of distilling tower |
|---|---|---|---|
| unit: /hr | 38.5 kg | 32.9 kg | 0.26 kg |
| Cr(2EHA)$_3$ (ppm) | 3.0 | 3.5 | 134 |
| 2,5-dimethyl-pyrrole (ppm) | 3.6 | 4.2 | 159 |
| Triethyl aluminum (ppm) | 28.4 | 33.0 | 1272 |
| Tetrachloro-ethane (ppm) | 5.2 | 6.1 | 234 |
| Heptane (wt %) | 66.9 | 78.4 | 0.0 |
| Ethylene (wt %) | 14.6 | 0.0 | 0.0 |
| C6 components (wt %) | 17.8 | 20.8 | 0.0 |
| High-boiling components (wt %) | 0.60 | 0.70 | 89.4 |
| Polyethylene (ppm) | 700 | 820 | 10.43 wt % |
| Total | 100.0 | 100.0 | 100.0 |

|  | Evaporated component from evaporator | Concentrated component from evaporator |
|---|---|---|
| unit: /hr | 0.23 kg | 27.3 g |
| Cr(2EHA)$_3$ (ppm) | 0.0 | 0.127 wt % |
| 2,5-dimethyl-pyrrole (ppm) | 177.7 | 0.0 |
| Triethyl aluminum (ppm) | 0.0 | 1.20 wt % |
| Tetrachloro-ethane (ppm) | 261.2 | 0.0 |
| Heptane (wt %) | 0.0 | 0.0 |
| Ethylene (wt %) | 0.0 | 0.0 |
| C6 components (wt %) | 0.0 | 0.0 |
| High-boiling components (wt %) | 100.0 | 0.0 |
| Polyethylene (ppm) | 0.0 | 98.7 wt % |
| Total | 100.0 | 100.0 |

Note:
Content of 1-hexene in C6 components: 99.5% by weight, Molar ratio of 1-hexene to ethylene: 0.41, Catalytic efficiency: 546,636 g-1-hexene/g-chromium

Example 21

The same procedure for continuous oligomerization of ethylene as defined in Example 19 was conducted except that octanoic acid (2-ethyl-hexanoic acid) as a metal-solubilizing agent was continuously fed into the degassing tank. The amount of the metal-solubilizing agent was adjusted such that the concentration thereof in the reaction solvent was 0.022% by weight.

The reaction solution was sampled from the bottom of the product-distilling tower to analyze deposited metal components and then, no deposited metal components were substantially observed. Incidentally, in the analysis of the deposited metal components, the sampled solution was passed through a filter paper (5A) and then the surface of the filter paper was washed with n-heptane and then further washed with an 10 wt % aqueous solution of nitric acid. Concentrations of metal components in the aqueous nitric acid solution were measured by a high-frequency plasma emission spectroscopic analyzing method. The mass balance in the afore-mentioned process are shown in Table 5. The evaporator was also operated in the same good condition as in Example 19.

TABLE 5

|  | Reaction solution | Degassed solution | Solution from bottom of distilling tower |
|---|---|---|---|
| unit: /hr | 42.5 kg | 36.3 kg | 0.35 kg |
| Cr(2EHA)$_3$ (ppm) | 3.0 | 3.5 | 363 |
| 2,5-dimethyl-pyrrole (ppm) | 3.6 | 4.2 | 430 |
| Triethyl aluminum (ppm) | 28.4 | 33.0 | 3443 |
| Hexachloro-ethane (ppm) | 7.4 | 8.6 | 892 |
| Heptane (wt %) | 62.1 | 72.7 | 0.0 |
| Ethylene (wt %) | 14.6 | 0.0 | 0.0 |
| C6 components (wt %) | 22.5 | 26.3 | 0.0 |
| High-boiling components (wt %) | 0.75 | 0.88 | 90.8 |
| Polyethylene (ppm) | 800 | 936 | 8.71 wt % |
| Total | 100.0 | 100.0 | 100.0 |

|  | Evaporated component from evaporator | Concentrated component from evaporator |
|---|---|---|
| unit: /hr | 0.32 kg | 31.9 g |
| Cr(2EHA)$_3$ (ppm) | 0.0 | 0.399 wt % |
| 2,5-dimethyl-pyrrole (ppm) | 473.4 | 0.0 |
| Triethyl aluminum (ppm) | 0.0 | 3.79 wt % |
| Hexachloro-ethane (ppm) | 981.4 | 0.0 |
| Heptane (wt %) | 0.0 | 0.0 |
| Ethylene (wt %) | 0.0 | 0.0 |
| C6 components (wt %) | 0.0 | 0.0 |

TABLE 5-continued

| | | |
|---|---|---|
| High-boiling components (wt %) | 99.9 | 0.0 |
| Polyethylene (ppm) | — | 95.8 wt % |
| Total | 100.0 | 100.0 |

Note:
Content of 1-hexene in C6 components: 99.5% by weight, Molar ratio of 1-hexene to ethylene: 0.51, Catalytic efficiency: 690,972 g-1-hexene/g-chromium Example 22

The same procedure for continuous oligomerization of ethylene as defined in Example 19 was conducted except that the reaction temperature and the reaction pressure were changed to 120° C. and 70 kg/cm$^2$G, respectively. The mass balance in the afore-mentioned Example are shown in Table 6. The evaporator was also operated in a good condition as in Example 19.

TABLE 6

| | Reaction solution | Degassed solution | Solution from bottom of distilling tower |
|---|---|---|---|
| unit: /hr | 52.3 kg | 40.4 kg | 1.06 kg |
| Cr(2EHA)$_3$ (ppm) | 3.0 | 3.9 | 44 |
| 2,5-dimethyl-pyrrole (ppm) | 3.6 | 4.6 | 52 |
| Triethyl aluminum (ppm) | 28.4 | 37.0 | 419 |
| Hexachloro-ethane (ppm) | 5.2 | 6.8 | 77 |
| Heptane (wt %) | 40.3 | 52.1 | 0.0 |
| Ethylene (wt %) | 22.7 | 0.0 | 0.0 |
| 1-hexene (wt %) | 35.0 | 45.3 | 0.0 |
| High-boiling components (wt %) | 1.90 | 2.46 | 93.3 |
| Polyethylene (ppm) | 1350 | 1746 | 6.63 wt % |
| Total | 100.0 | 100.0 | 100.0 |

| | Evaporated component from evaporator | Concentrated component from evaporator |
|---|---|---|
| unit: /hr | 0.99 kg | 71.1 g |
| Cr(2EHA)$_3$ (ppm) | 0.0 | 0.066 wt % |
| 2,5-dimethyl-pyrrole (ppm) | 56.1 | 0.0 |
| Triethyl aluminum (ppm) | 0.0 | 0.63 wt % |
| Hexachloro-ethane (ppm) | 82.5 | 0.0 |
| Heptane (wt %) | 0.0 | 0.0 |
| Ethylene (wt %) | 0.0 | 0.0 |
| 1-hexene (wt %) | 0.0 | 0.0 |
| High-boiling components (wt %) | 100.0 | 0.0 |
| Polyethylene (ppm) | 0.0 | 99.3 wt % |
| Total | 100.0 | 100.0 |

Examples 23 to 26

The same procedures for continuous oligomerization of ethylene as defined in Example 21 were conducted except that 1-hexanol (Example 23), hexylamine (Example 24), ammonia (Example 25) and acetylacetone (Example 26) were used as the metal solubilizing agent. As a result, it was found that in all of Examples 23 to 26, the evaporator was also operated in a good condition as in Example 21. The reaction solutions were sampled from the bottom of the product-distilling tower in the same manner as in Example 21. The analysis for the deposited metal components revealed that no deposited metal components were substantially observed in any of Examples.

What is claimed is:

1. A continuous process for producing an α-olefin oligomer by subjecting an α-olefin to oligomerization in a reaction zone in the presence of a reaction solution containing a chromium-based catalyst, which process comprises continuously conducting said oligomerization of α-olefin using said chromium-based catalyst formed from at least a chromium compound (a), a nitrogen-containing compound (b) selected from the group consisting of amines, amides and imides, and an alkyl aluminum compound (c) while maintaining the molar ratio of the α-olefin oligomer to α-olefin in the range of 0.05 to 1.00 while simultaneously forming said chromium-based catalyst during oligomerization of the α-olefin.

2. A process according to claim 1, wherein the concentration of α-olefin in the reaction solution in the reaction zone is not less than 0.5 mol/l.

3. A process according to claim 1, wherein the residence time of the reaction solution in the reaction zone is not more than 60 minutes.

4. A process according to claim 1, wherein the catalyst is continuously fed into the reaction zone such that the concentration of chromium in the reaction solution in the reaction zone is maintained at not more than 1 ppm.

5. A process according to claim 1, wherein the oligomerization of α-olefin is conducted under the reaction conditions which satisfy the formulae (1) and (2):

$$T \geq 105° C. \quad (1)$$

$$p > 0.5T - 15 \quad (2)$$

where T represents a reaction temperature (° C) and P represents a reaction pressure (kg/cm$^2$G(Gauge)).

6. A process according to claim 1, wherein the molar ratio between the chromium compound (a), the nitrogen-containing compound (b) selected from the group consisting of amines, amides and imides and the alkyl aluminum compound (c) when used in the formation of the chromium-based catalyst, (a) (b):(c), is 1:0.1 to 10:1 to 100.

7. A process according to claim 1, wherein said chromium-based catalyst is formed from at least the chromium compound (a), the nitrogen-containing compound (b) selected from the group consisting of amines, amides and imides, the alkyl aluminum compound (c) and a halogen-containing compound (d).

8. A process according to claim 7, wherein the molar ratio between the chromium compound (a), the nitrogen-containing compound (b) selected from the group consisting of amines, amides and imides, the alkyl aluminum compound (c) and the halogen-containing compound (d) when used in the preparation of the chromium-based catalyst, (a):(b):(c):(d), is 1: 0.1 to 10: 1 to 100: 0.1 to 20.

9. A process according to claim 7, wherein said halogen-containing compound (d) contains an element selected from the group consisting of the 3-, 4-, 5-, 6-, 13-, 14- and 15-Groups of the Periodic Table.

10. A process according to claim 1, wherein the oligomerization of α-olefin is conducted in such a manner that before the α-olefin, the chromium compound (a), the nitrogen-containing compound (b) selected from the group consisting of amines, amides and imides and the alkyl aluminum compound (c) come into contact with each other, the chromium compound and the alkyl aluminum compound do not previously contact each other.

11. A process according to claim 1, wherein the oligomerization of α-olefin is conducted by using a continuous stirring tank reactor.

12. A process according to claim 1, wherein the oligomerization of α-olefin is conducted by using a loop-type reactor.

13. A process according to claim 1, wherein the oligomerization of α-olefin is conducted by using a gas-stripping-type reactor.

14. A process according to claim 1, wherein the oligomerization of α-olefin is conducted by using a gas-bubble column-type reactor.

15. A process according to claim 1, wherein the oligomerization of α-olefin is conducted by using a tubular reactor.

16. A process according to claim 1, wherein the α-olefin is ethylene and the α-olefin oligomer comprises 1-hexene.

* * * * *